United States Patent
Guan et al.

(10) Patent No.: US 8,277,544 B2
(45) Date of Patent: Oct. 2, 2012

(54) THERMAL MODULATION DEVICE FOR TWO DIMENSIONAL GAS CHROMATOGRAPHY

(75) Inventors: Xiaosheng Guan, Beijing (CN); Qiang Xu, Shanghai (CN)

(73) Assignee: Agilent Technologies, Inc., Santa Clara, CA (US)

( * ) Notice: Subject to any disclaimer, the term of this patent is extended or adjusted under 35 U.S.C. 154(b) by 372 days.

(21) Appl. No.: 12/732,288

(22) Filed: Mar. 26, 2010

(65) Prior Publication Data

US 2011/0232366 A1  Sep. 29, 2011

(51) Int. Cl.
    *B01D 53/02* (2006.01)
(52) U.S. Cl. ............ 96/101; 96/103; 96/104; 96/106; 95/87; 73/23.35; 73/23.42
(58) Field of Classification Search ............ 96/101, 96/103, 104, 105, 106; 95/82, 87; 73/23.35, 73/23.41, 23.42
    See application file for complete search history.

(56) References Cited

U.S. PATENT DOCUMENTS

| | | | |
|---|---|---|---|
| 5,135,549 A * | 8/1992 | Phillips et al. | 95/8 |
| 5,596,876 A * | 1/1997 | Manura et al. | 62/55.5 |
| 6,547,852 B2 * | 4/2003 | Ledford et al. | 95/87 |
| 6,838,288 B2 * | 1/2005 | Beens | 436/161 |
| 7,284,409 B2 * | 10/2007 | Hasselbrink et al. | 73/23.42 |
| 7,293,449 B2 * | 11/2007 | Hasselbrink et al. | 73/23.42 |
| 7,490,506 B2 * | 2/2009 | Chaintreau et al. | 73/23.41 |
| 2003/0100124 A1 | 5/2003 | Beens | |
| 2009/0207249 A1 | 8/2009 | Erel et al. | |
| 2009/0253181 A1 * | 10/2009 | Vangbo et al. | 435/91.1 |
| 2011/0005932 A1 * | 1/2011 | Jovanovich et al. | 204/453 |
| 2011/0088452 A1 * | 4/2011 | Kim et al. | 73/23.42 |

FOREIGN PATENT DOCUMENTS

AU  199748570 B2  11/1997

OTHER PUBLICATIONS

Philip J. Marriott et al., "Longitudinally Modulated Cryogenic System. A Generally Applicable Approach to Solute Trapping and Mobilization in Gas Chromatography", Analytical Chemistry, vol. 69, No. 13, Jul. 1, 1997, pp. 2582-2588.
Russell M. Kinghorn et al., "Design and implementation of Comprehensive Gas Chromatography with Cryogenic Modulation", J. High Resol. Chromatogr. 2000, vol. 23, No. 3, pp. 245-252.

* cited by examiner

Primary Examiner — Robert Clemente

(57) ABSTRACT

A thermal modulation device for a gas chromatography (GC) system a cold zone, a first hot zone and a second hot zone, which are located outside of a GC oven of the GC system, and a flexible capillary column. The cold zone includes a thermoelectric cooler assembly. The first hot zone is adjacent a first side of the cold zone, and has a corresponding first heat source. The second hot zone is adjacent a second side of the cold zone, and has a corresponding second heat source. The flexible capillary column includes a first segment, configured to move between the first hot zone and the cold zone in accordance with a modulation frequency, and a second segment, configured to move between the cold zone and the second hot zone in accordance with the modulation frequency.

20 Claims, 3 Drawing Sheets

THERMAL MODULATION DEVICE FOR TWO DIMENSIONAL GAS CHROMATOGRAPHY

BACKGROUND

Gas chromatography (GC) is used to separate solutes or components in an analyte sample (vapor) for measurement. A gas chromatography mass spectrometer (GC-MS) is an implementation in which the GC device provides molecular samples in gaseous form to an inlet of the MS device. Generally, a GC device includes capillary column(s) for separating the solutes. The columns are typically made of metal, glass or quartz, for example, and coated on the inside with a thin-film coating or stationary phase. The GC process consists of introducing the analyte sample into a column using a continuous flow of carrier gas, such as hydrogen or helium. Various solutes within the sample react differently with the stationary phase, and thus move at different speeds through the column, resulting in separation of the solutes. The separated solutes may then be detected by various detectors or provided as input to a mass spectrometer.

Two-dimensional GC (2D-GC) systems include two columns, arranged in series, having different dimensions and/or different stationary phases. This allows for additional separation of the solutes in the sample under different conditions, which is particularly effective for solutes having similar reactions to the first stationary phase. Two-dimensional GC systems include modulators, which trap and accumulate solutes from the first capillary column, while compounds from the second capillary column are being analyzed. Two-dimensional GC systems may have either flow based or thermal based modulators. Typically, conventional flow based 2D-GC modulators are relatively small in size and do not need cryogens or other cooling means for operation. However, flow based 2D-GC modulators use about ten times more carrier gas, all of which flows out of the second dimension column. Therefore, in 2D-GC-MS applications, for example, column flow must be split prior to the mass spectrometer, allowing only about 1/10 of the carrier gas into the mass spectrometer, and thus causing a reduction of detection sensitivity.

Conventional thermal based 2D-GC modulators typically introduce at least one non-moving cryogenic gas jet into a hot GC oven, usually impinging at the starting segment of second dimension capillary column to affect solute trapping. Examples of conventional thermal based 2D-GC modulators include dual jet design, quad-jet design including two cold jets and two hot jets, and loop modulator design including one cold jet and one hot jet. Conventional cryogenic thermal modulators are also provided with moving mechanisms, such as a moving cryogenic modulator, a semi-rotating cryogenic modulator, and a longitudinally modulated cryogenic system (LMCS), which is described for example, by MARRIOTT in Australian Patent No. AU 199748570, "Apparatus and/or Device for Concentration."

However, even though only a small segment of a capillary column is to be cryogenically cooled in thermal modulator designs, the conventional thermal based 2D-GC GC modulators perform cooling inside the hot GC oven, so that the ambient heat of the GC oven may be used to effect solute remobilization (e.g., before and after cooling). Accordingly, large amounts of gas jet at a very low temperatures must be produced, most of which is needed simply to nullify the heat of the surrounding hot GC oven. Production of cold gas jets may be either from insulated tanks storing large amounts of cryogenic fluids (e.g., liquid nitrogen, liquid carbon dioxide and the like), or with a refrigeration system having substantial cooling power. The conventional 2D-GC modulators are therefore bulky in overall size, and consume extensive amounts of power and cryogens.

BRIEF DESCRIPTION OF THE DRAWINGS

The illustrative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
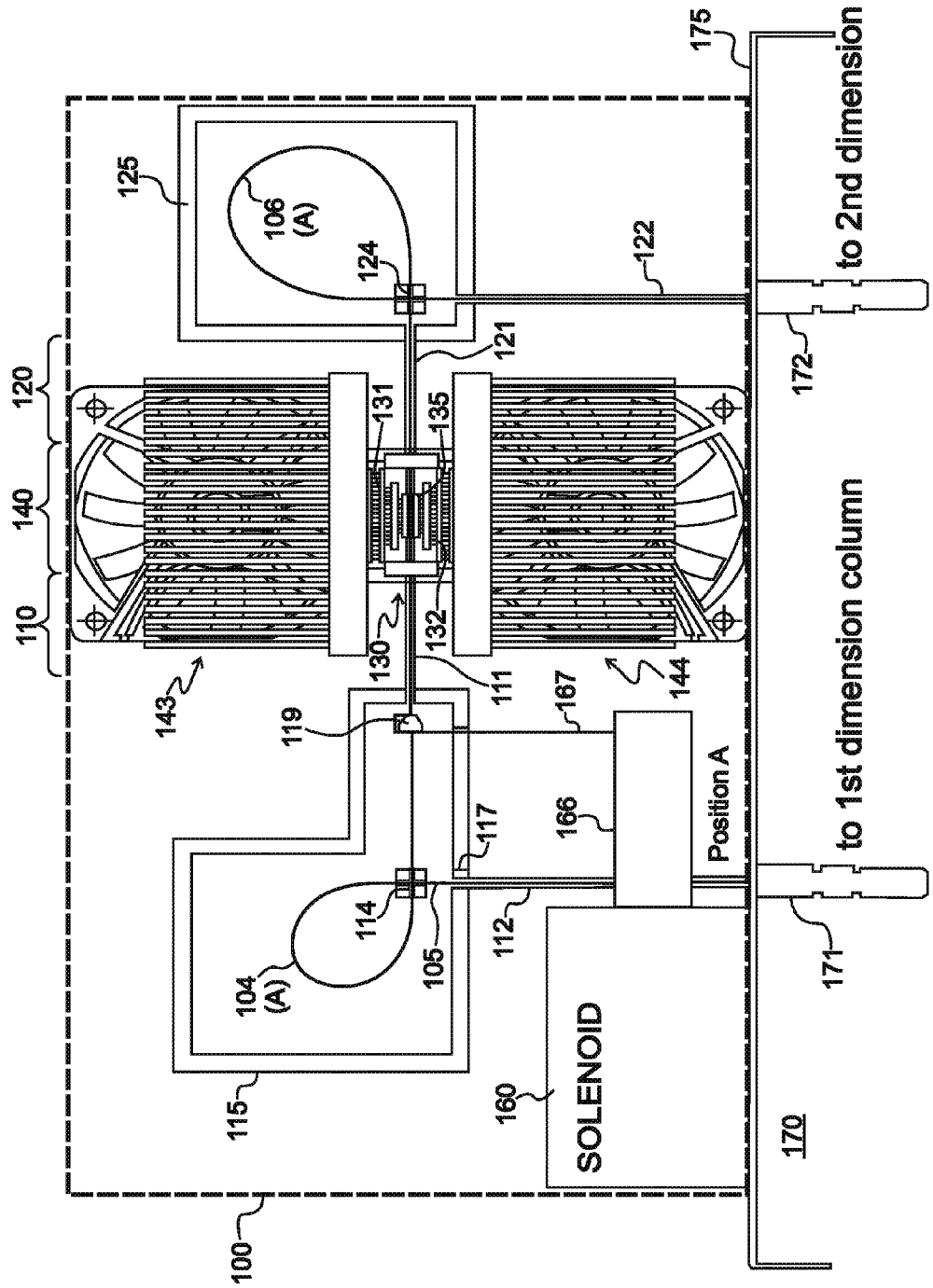
FIG. 1 is a block diagram illustrating a thermal modulator for a two-dimensional gas chromatography system, according to a representative embodiment.

In the following detailed description, for purposes of explanation and not limitation, illustrative embodiments disclosing specific details are set forth in order to provide a thorough understanding of embodiments according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as not to obscure the description of the example embodiments. Such methods and devices are within the scope of the present teachings.

Generally, it is understood that the drawings and the various elements depicted therein are not drawn to scale. Further, relative terms, such as "above," "below," "top," "bottom," "upper," "lower," "left," "right," "vertical" and "horizontal," are used to describe the various elements' relationships to one another, as illustrated in the accompanying drawings. It is understood that these relative terms are intended to encompass different orientations of the device and/or elements in addition to the orientation depicted in the drawings. For example, if the device were inverted with respect to the view in the drawings, an element described as "above" another element, for example, would now be "below" that element. Likewise, if the device were rotated 90 degrees with respect to the view in the drawings, an element described as "vertical," for example, would now be "horizontal."

Generally, various representative embodiments provide a compact dual-stage thermal modulator for a 2D-GC system, which requires no cryogenic fluids or associated logistics, and no large refrigeration system. Since it is thermal based, a mass spectrometer can be used in conjunction with the various embodiments without sacrificing detection sensitivity. Also, the compact size of the thermal modulator enables portable (e.g., out-of-lab) use for 2D-GC and 2D-GC-MS analyses.

Figure 2:
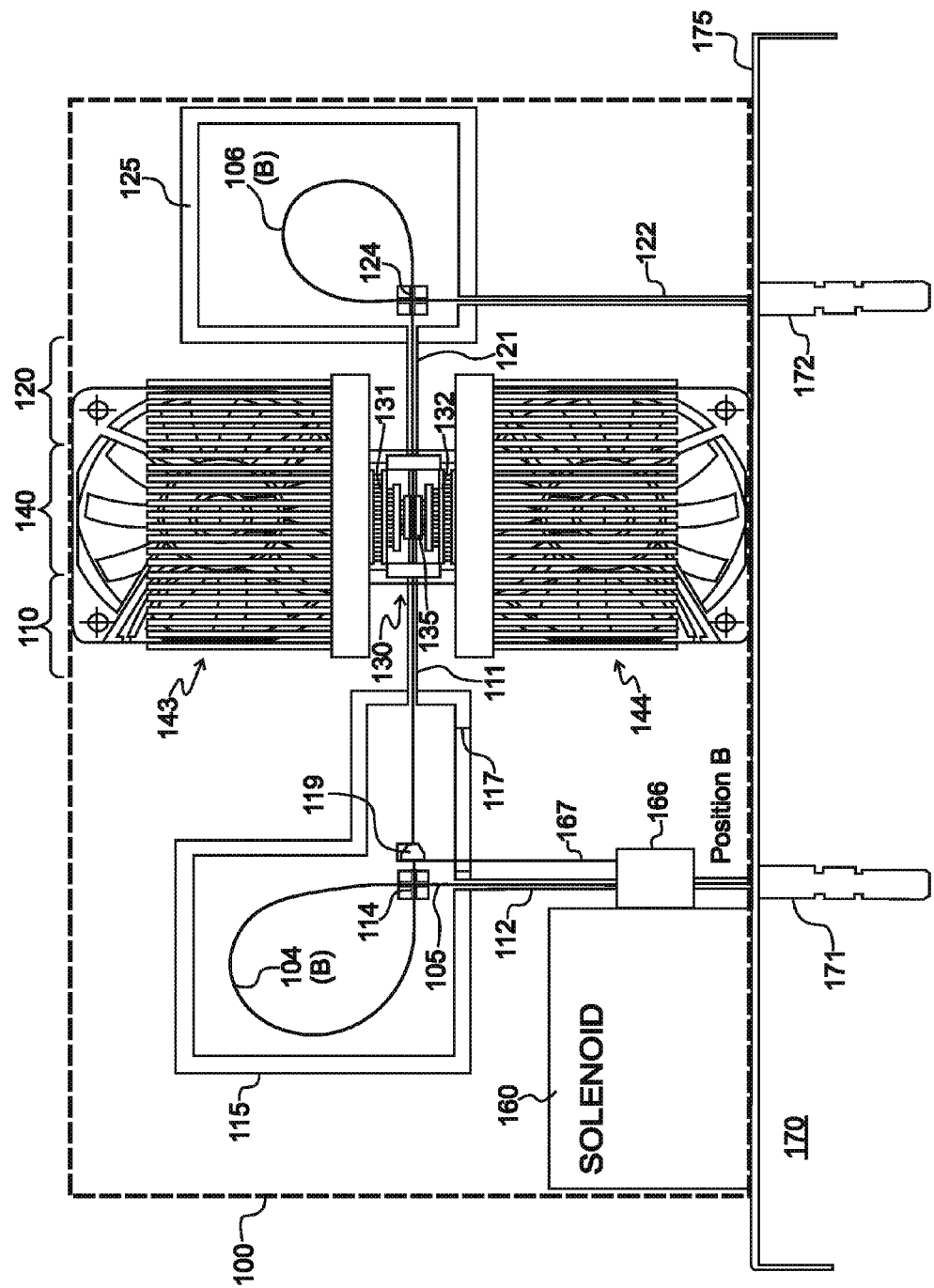
FIG. 2 is a block diagram illustrating a thermal modulator for a two-dimensional gas chromatography system, according to a representative embodiment.

FIG. 1 is a block diagram illustrating a thermal modulator for a 2D-GC system, according to a representative embodiment, in which a solenoid rod is in an extended position. FIG. 2 is a block diagram illustrating the thermal modulator for a 2D-GC system, according to a representative embodiment, in which the solenoid rod is in a retracted position.

Referring to FIGS. 1 and 2, a dual-stage thermal modulator 100 for a 2D-GC system includes first hot zone 110, second hot zone 120 and cold zone 140 located between the first and second hot zones 110 and 120. The thermal modulator 100 enables reciprocating movement of a capillary column 105 in and out of the cold zone 140 at a predetermined modulation frequency.

The thermal modulator 100 is located outside GC oven 170 of the corresponding 2D-GC system, as indicated by the exterior oven wall 175. The first and second dimension columns are located within the GC oven 170, and are respectively connected to metal tubes 112 and 122 of the thermal modulator 100 through corresponding connectors 171 and 172 for serial communication with the capillary column 105. In the depicted embodiment, each of the connectors 171 and 172 is shown as a union fastened by two nuts, although other types of connections compatible with GC technology may be incorporated.

The cold zone 140 is created by a thermoelectric cooler assembly, which includes enclosed cooling portion 130, and first and second fan-heatsinks 143 and 144 corresponding to first and second Peltier devices 131 and 132 housed in the enclosed cooling portion 130. For clarity, the enclosed cooling portion 130 is shown in more detail in FIG. 3, which is a block diagram illustrating a blown-up portion of the thermal modulator 100, according to a representative embodiment. In various embodiments, thermoelectric cooling means other than Peltier devices may be incorporated, without departing from the scope of the present teachings.

The cold zone 140 includes a cooling block 135 sandwiched between the first and second Peltier devices 131 and 132. In an embodiment, the first and second Peltier devices 131 and 132 are three-stage Peltier devices, for example, although various stage Peltier devices may be incorporated. The first fan-heatsink 143 includes a first heatsink abutting the first Peltier device 131 and a corresponding first fan, which draws heat away from the first heat sink and thus the first Peltier device 131. Likewise, the second fan-heatsink 144 includes a second heatsink abutting the second Peltier device 132 and a corresponding second fan, which draws heat away from the second heatsink and thus the second Peltier device 132.

In various embodiments, the cold zone 140 may incorporate various alternative configurations without departing from the scope do the present teachings. For example, the cold zone 140 may include a single Peltier device and corresponding cooling unit (e.g., heatsink and fan combination). Likewise, the first and second Peltier devices 131 and 132 may have a number of stages other than three. Also, the first and second Peltier devices 131 and 132 and/or the corresponding cooling units may be replaced by other types of cooling devices and/or cooling units, such as portable free-piston-sterling-cooler (FPSC) devices, which provide higher efficiency and/or lower temperatures. Also, in various embodiments, the cold zone 140 may be implemented using techniques other than thermoelectric cooling, such as refrigerant cooling or cryogenic cooling (e.g., using carbon dioxide or nitrogen), although thermoelectric cooling is generally more compact and efficient.

Figure 3:
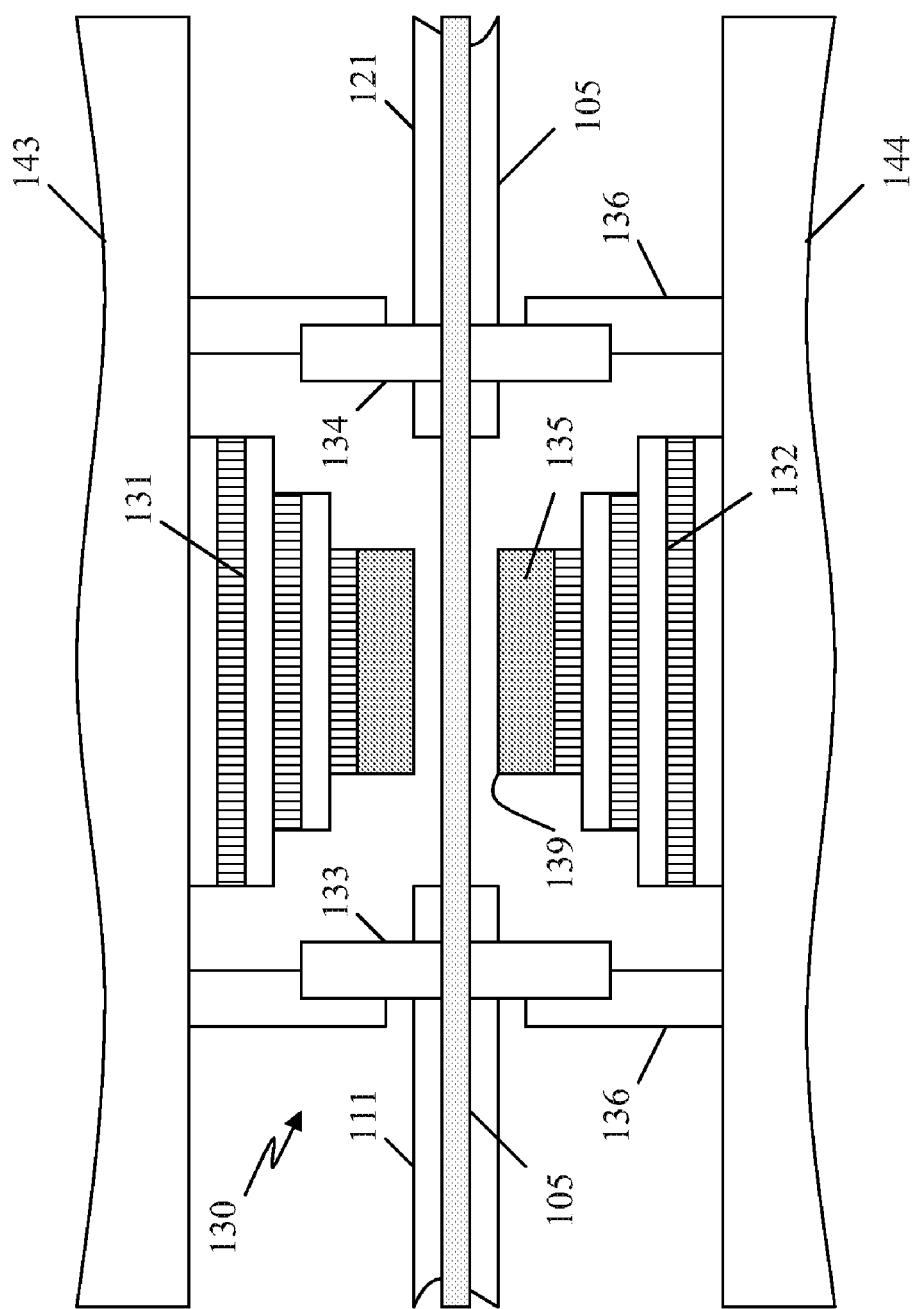
FIG. 3 is a block diagram illustrating a portion of a cold zone of a thermal modulator for a two-dimensional gas chromatography system, according to a representative embodiment.

Referring to FIG. 3, the cooling block 135 is formed of a highly conductive heat transfer material, including various metals, such as copper or aluminum, for example. When formed of copper, for example, the cooling block 135 is relatively thin, having a thickness dimension of about 3 mm, for example. The cooling block 135 includes a through-hole 139 traversing its length longitudinally, having an inner diameter of about 0.2 mm to about 0.4 mm, for example. In an embodiment, the first and second Peltier devices 131 and 132 abut the cooling block 135 on opposite sides (e.g., top and bottom) in order to draw heat from the sample passing though the through-hole 139, via the capillary column 105, discussed below.

An enclosure 136 houses the first and second Peltier devices 131 and 132 and the cooling block 135. The enclosure 136 is clamped tight between the first and second fan-heatsinks 143 and 144 using a clamping mechanism (not shown), such as O-rings and/or screw-nut sets, for example. The clamping mechanism also ensures that first and second fan-heatsinks 143 and 144 are in good contact with the first and second Peltier devices 131 and 132, respectively. The enclosure 136 has two holes on opposing sides that substantially align with the end openings of the through-hole 139 in the cooling block 135. The two holes in the enclosure 136 are capped with corresponding septums 133 and 134. In various embodiments, the enclosure 136 may include ports (not shown) through which electric cables pass for providing power and control for thermoelectric cooling. Also, in various embodiments, the enclosure 136 may include a port (not shown) connected to a pure nitrogen source for providing a small purging flow into the enclosure 136 to prevent or reduce condensation.

Referring again to FIGS. 1 and 2, the thermal modulator 100 further includes the first and second hot zones 110 and 120 on either side of the cold zone 140. The first hot zone 110 includes first heated tube 111 and the second hot zone 120 includes second heated tube 121, each of which is formed of an efficient heat conducting material, including various metals, such as copper or aluminum, for example.

The first heated tube 111 has one end contacting first heated block 115 and an opposite end inserted through the septum 133 of the enclosure 136, such that the first heated tube 111 is substantially aligned with the through-hole 139 in the cooling block 135. Likewise, the second heated tube 121 has one end contacting second heated block 125 and an opposite end inserted through the septum 134 of the enclosure 136, such that the second heated tube 121 is substantially aligned with the opposite end of the through-hole 139 in the cooling block 135. The septums 133 and 134 seal the outer surfaces of the first and second heated tubes 111 and 121. The sealing helps to isolate the interior of the enclosure 136, and also forces purging nitrogen gas to exit only through appropriate openings, such as annular spaces between the first and second heated tubes 111 and 121 and the capillary column 105, discussed below.

In an embodiment, the first heated tube 111 is heated by conduction through its contact with the first heated block 115. The first heated tube 111 maintains a temperature in a range of about 30° C. to about 350° C., for example, although the desired temperature ranges may vary to provide unique benefits for any particular situation or to meet application specific design requirements of various implementations, as would be apparent to one of ordinary skill in the art. Alternatively, the first heated tube 111 may be heated separately through a dedicated heat source, such as an electric wire coil wrapped around at least a portion of the longitudinal length of the first heated tube 111 between the first heated block 115 and the enclosure 136, without departing from the scope of the present teachings. In an embodiment, the opposite end of the first heated tube 111 inserted through the septum 133 is not in contact with the cooling block 135, as shown in FIG. 3, which prevents direct heat transfer from the first heated tube 111 to the cooling block 135.

Similarly, in an embodiment, the second heated tube 121 is heated by conduction through its contact with the second heated block 125. The second heated tube 121 maintains a temperature in a range of about 30° C. to about 350° C., for example, although the desired temperature ranges may vary to provide unique benefits for any particular situation or to meet application specific design requirements of various implementations, as would be apparent to one of ordinary skill in the art. Alternatively, the second heated tube 121 may be heated separately through a dedicated heat source, such as an electric wire coil wrapped around at least a portion of the longitudinal length of the second heated tube 121 between the second heated block 125 and the enclosure 136, without departing from the scope of the present teachings. In an embodiment, the opposite end of the second heated tube 121 inserted through the septum 134 is not in contact with the cooling block 135, as shown in FIG. 3, which prevents direct heat transfer from the second heated tube 121 to the cooling block 135.

In various embodiments, the second heated tube 121 may be the same length as or a different length than the first heated tube 111, depending of the particular situation or application specific design requirements of various implementations, as would be apparent to one of ordinary skill in the art. Generally, a second capillary segment of the capillary column 105 located within the second heated tube 121 and a first capillary segment capillary column 105 located within the first heated tube 111 can be alternately moved into and out of the cold zone 140 by solenoid 160, in accordance with a thermal modulation frequency, as discussed below.

The first and second heated blocks 115 and 125 may be formed of an efficient heat conducting material, such as aluminum or copper, for example. In an embodiment, each of the first and second heated blocks 115 and 125 includes a dedicated electric heater (not shown) connected to one or more of the corresponding sides. Since they are located outside of the oven wall 175, neither the first and second heated blocks 115 and 125 nor the first and second heated tubes 111 and 121 are heated ambiently by the oven 170. However, various alternative embodiments may include heating one or more of the first and second heated blocks 115 and 125 and the first and second heated tubes 111 and 121 using heat bled from the oven 170. In various embodiments, the first and second heated blocks 115 and 125 may operate in isothermal or temperature ramped modes, for example.

Also, in various embodiments, the first and second heated blocks 115 and 125 may be implanted as a single heated block and corresponding electric heater for heating both the first and second heated tubes 111 and 121. For example, the single heated block may have separate protrusions, substantially corresponding to the depicted configuration of the first and second heated blocks 115 and 125, where a first protrusion contacts the first heated tube 111 and a second protrusion contacts the second heated tube 121 to provide conduction heating, respectively.

The first and second heated blocks 115 and 125 maintain temperatures in a range of about 30° C. to about 350° C., for example, although the desired temperature ranges may vary to provide unique benefits for any particular situation or to meet application specific design requirements of various implementations, as would be apparent to one of ordinary skill in the art. Accordingly, the first and second heated blocks 115 and 125 heat portions of the capillary column 105 not located in the first or second heated tubes 111 and 121, respectively. This assures that there are no cold spots in the capillary column 105 and that the solutes remain mobilized. In various embodiments, the first and second heated blocks 115 and 125 may have different shapes to meet application specific design requirements of various implementations, as would be apparent to one of ordinary skill in the art.

As stated above, the metal tube 112 is connected between the first dimension column at the oven wall 175 and the first heated block 115, and the metal tube 122 is connected between the second dimension column at the oven wall 175 and the second heated block 125. The capillary column 105 passes from the first dimension column through the metal tube 112 into an interior portion of the first heated block 115. The capillary column 105 then extends through the first heated tube 111 of the first hot zone 110, through the through-hole 139 in the cooling block 135 of the cold zone 140, and through the second heated tube 121 of the second hot zone 120 into an interior portion of the second heated block 125. The capillary column 105 then passes from the interior portion of the second heated block 125 through the metal tube 122 to the second dimension column at the oven wall 175. The first and second heated blocks 115 and 125 may include fixtures 114 and 124, respectively, for securing the capillary column 105.

As shown in FIG. 1, the capillary column 105 forms a first loop 104 inside the first heated block 115 and a second loop 106 inside the second heated block 125. The first and second loops 104 and 106 are complementary to one another, increasing and decreasing in size to accommodate movement of the capillary column 105 within the first hot zone 110, the second hot zone 120 and the cold zone 140. For example, FIG. 1 shows loop size (A) of the first and second loops 104 and 106, and FIG. 2 shows loop size (B) of the first and second loops 104 and 106, as discussed below. In addition, although depicted as single loops, it is understood that the first and second loops 104 and 106 may consist of multiple loops of the capillary column 105, without departing from the scope of the present teachings.

The capillary column 105 is generally flexible, and may be formed of fused silica having an exterior polyimide protection layer, for example. Each of the metal tubes 112 and 122 may have an inner diameter in range of about 0.8 mm to about 2.0 mm, for example, to facilitate the manufacturing process and installation of the capillary column 105 through them.

The first and second heated tubes 111 and 121 each have an inner diameter that substantially corresponds to the inner diameter of the through-hole 139 in the cooling block 135, e.g., about 0.2 mm to about 0.4 mm, although the inner diameters may vary to provide unique benefits for any particular situation or to meet application specific design requirements of various implementations, as would be apparent to one of ordinary skill in the art. The inner diameter of each is large enough to allow the flexible capillary column 105 to slide linearly within the first and second heated tubes 111 and 121, and the through-hole 139, respectively. In an embodiment, there may be an annular space between the capillary column 105 and the interior walls of the first and second heated tubes 111 and 121, and/or the through-hole 139. The annular space provides a channel for purging nitrogen flow from the enclosed thermal modulator 100 to an exit or purge port (not shown), hence blocking humidity from the thermal modulator 100 and eliminating condensation.

The thermal modulator 100 also includes the solenoid 160, which has a movable rod 166. A gripper 167 extends from a distal end of the rod 166 through slot 117 in the bottom of the first heated block 115, and connects to the capillary column 105 by means of metal ferrule 119 or other type connection. In the depicted embodiment, operation of the solenoid 160 moves the rod 166 linearly back and forth (e.g., left and right), and the gripper 167 translates the back and forth movement to the capillary column 105 inside the first heated block 115.

For example, when the solenoid 160 is energized (activated), the rod 166 moves outward (e.g., to the right) to Position A, causing the capillary column 105 to move to the right by substantially the same amount of movement. This causes a first capillary segment located in the first hot zone 110 to slide from the first heated tube 111 into the cooling block 135 of the cold zone 140. A second capillary segment, initially located in the cooling block 135 of the cold zone 140, simultaneously slides from the cooling block 135 into the second heated tube 121 in the second hot zone 120.

The end position of this movement is depicted in FIG. 1, for example, which shows the rod 166 in the out position (Position A). In this example, the loop size (A) of the first loop 104 in the first heated block 115 is smaller than the loop size (A) of the second loop 106 in the second heated block 125, indicating that the amount of capillary column 105 within the first heated block 115 decreases as the first capillary segment moves into the cooling block 135, and that the amount of the capillary column 105 within the second heated block 125 correspondingly increases as the second capillary segment moves out of the cooling block 135.

When the solenoid 160 is de-energized (de-activated), the rod 166 moves inward (e.g., to the left) to Position B, causing the capillary column 105 to move to the left by substantially the same amount of movement. This causes the capillary segment located in the second hot zone 120 to slide from the second heated tube 121 into the cooling block 135 of the cold zone 140. The first capillary segment, located in the cooling block 135 of the cold zone 140 from the previous activation of the solenoid 160, simultaneously slides from the cooling block 135 into the first heated tube 111 in the first hot zone 110.

This movement is depicted in FIG. 2, for example, which shows the rod 166 in the in position (Position B). In this example, the loop size (B) of the first loop 104 in the first heated block 115 is now larger than the loop size (B) of the second loop 106 in the second heated block 125, indicating that the amount of capillary column 105 within the first heated block 115 increases as the first capillary segment moves out of the cooling block 135, and that the amount of the capillary column 105 within the second heated block 125 correspondingly decreases as the second capillary segment moves into the cooling block 135. As stated above, although depicted as single loops, it is understood that the first and second loops 104 and 106 may consist of multiple loops of the capillary column 105, without departing from the scope of the present teachings.

In the embodiment of FIGS. 1 and 2, the solenoid 160 is depicted as a linear solenoid, for purposes of explanation. However, in various embodiments, the solenoid 160 may include other types of solenoids, such as a rotary solenoid, without departing from the scope of the present teachings. When the solenoid 160 is a rotary solenoid, for example, the rod 166 performs an arc movement in response to the solenoid 160 being energized/de-energized. This arc movement is translated to the capillary column 105 via the gripper 167 and the ferrule 119 in substantially the same manner as discussed above with respect to the linear movement of the rod 166, although the configuration of the capillary column 105, and first and second heated tubes 111 and 121, etc., would vary to account for the arcing motion, as would be apparent to one of ordinary skill in the art.

Alternatively, the rotary or arc movement may be translated to linear movement of capillary column 105 through various linkages and mechanisms, such as a cam, a rack and pinion, a crank-slider, and the like, as would be apparent to one of ordinary skill in the art. Also, the movement of the capillary column 105 may be actuated by various means other than a solenoid, such as linear or rotary motor, for example, without departing from the scope of the present teachings.

Accordingly, the thermal modulator 100 is a two-stage modulator. In the first stage (e.g., shown in FIG. 1), the first capillary segment slides from the first heated tube 111 into the cooling block 135 in response to movement of the solenoid rod 166 to Position A. Solutes in the sample located within the first capillary segment are therefore cryogenically trapped when in the cold zone 140. Meanwhile, solutes in the sample located within the second capillary segment, now positioned in the second heated tube 121, are remobilized, and will continue to flow toward the second dimension column. In other words, the movement of the solenoid rod 166 to Position A cryogenically traps solutes eluting from the first dimension column and releases trapped solutes into the second dimension column.

In the second stage (e.g., shown in FIG. 2), the second capillary segment slides from the second heated tube 121 into the cooling block 135 in response to movement of the solenoid rod 166 to Position B. Solutes in the sample located within the second capillary segment are therefore cryogenically trapped when in the cold zone 140. Meanwhile, solutes in the sample located within the first capillary segment, now positioned in the first heated tube 111, are remobilized. In other words, the movement of the solenoid rod 166 to Position B releases solutes trapped when the solenoid rod 166 was in Position A, and performs a second stage cryogenic trapping of the solutes being released from the first column segment.

The first and second column segments thus provide a dual-staged thermal modulator, which performs better in performance than a single stage thermal modulator, for example, because of reduced breakthrough during modulation. Further, as discussed above, the thermal modulation is performed outside the GC oven 170. Therefore, a relatively small amount of heating and cooling power is required to modulate only small segments of the capillary column 105, for example, as compared to conventional single and dual-staged thermal modulators. Accordingly, the thermal modulator 100 is able to be relatively compact in size, and may use efficient thermoelectric cooling processes.

The modulation frequency (or modulation period) of the thermal modulator 100 is controlled by controlling the cycle time of the solenoid 160. In an embodiment, operation of the solenoid 160 may be controlled by a dedicated controller (not shown), such as a processor, application specific integrated circuits (ASICs), field-programmable gate arrays (FPGAs), or combinations thereof. Thus, control may be implemented using software, firmware, hard-wired logic circuits, or combinations thereof. Alternatively, the solenoid 160 may be controlled by a common controller configured to control operations of the 2D-GC, as well as the solenoid 160. General operations the 2D-GC and the thermal modulator 100 are coordinated in order to provide the appropriate modulation frequency, as would be apparent to one of ordinary skill in the art.

In an embodiment, a processor may be configured to execute one or more logical or mathematical algorithms, including thermal modulation control via operation of the solenoid 160, and include a memory (e.g., nonvolatile memory) for storing executable software/firmware executable code that allows it to perform the various functions. The memory may be any number, type and combination of non-volatile read only memory (ROM) and volatile random access memory (RAM), and may store various types of information, such as signals and/or computer programs and software algorithms executable by the processor (and/or other components), e.g., to perform thermal modulation control of the embodiments described herein, as well as the basic functionality of the 2D-GC system. The memory may include any number, type and combination of tangible computer readable storage media, such as a disk drive, an electrically programmable read-only memory (EPROM), an electrically erasable and programmable read only memory (EEPROM), a universal serial bus (USB) drive, and the like.

Thus, according to various embodiments, a 2D-GC system may include a GC oven having an exterior oven wall and containing first and second dimension columns, and a dual-stage thermal modulator positioned outside the GC oven. The dual-stage thermal modulator may include a cooling block and at least one Peltier device abutting the cooling block, where the cooling block defines a through-hole having first and second end openings corresponding to first and second holes in the enclosure. The dual-stage thermal modulator may further include first and second heated tubes. The first heated tube has a corresponding first heat source, and is aligned with the end opening of the through-hole, such that a first segment of a capillary column passing through the first heated tube is able to move alternately between the first heated tube and the through-hole in the cooling block in accordance with a modulation frequency. The second heated tube has a corresponding second heat source, and is aligned with the second end opening of the through-hole, such that a second segment of the capillary column passing through the second heated tube is able to move alternately between the through-hole in the cooling block and the second heated tube in accordance with the modulation frequency. A solenoid, including a movable rod connected to the capillary column, controls the movement of the first and second segments of the capillary column. The capillary column is serially connected between the first dimension column and the second dimension column at the exterior oven wall.

While specific embodiments are disclosed herein, many variations are possible, which remain within the concept and scope of the invention. Such variations would become clear after inspection of the specification, drawings and claims herein. The invention therefore is not to be restricted except within the scope of the appended claims.

What is claimed is:

1. A thermal modulation device for a gas chromatography (GC) system, the device comprising:
    a cold zone located outside of a GC oven of the GC system, the cold zone comprising a thermoelectric cooler assembly;
    a first hot zone located outside of the GC oven of the GC system adjacent a first side of the cold zone, the first hot zone having a corresponding first heat source;
    a second hot zone located outside of the GC oven of the GC system adjacent a second side of the cold zone, the second hot zone having a corresponding second heat source; and
    a flexible capillary column comprising a first segment, configured to move between the first hot zone and the cold zone in accordance with a modulation frequency, and a second segment, configured to move between the cold zone and the second hot zone in accordance with the modulation frequency.

2. The device of claim 1, wherein the cold zone comprises a cooling block and at least one Peltier device abutting the cooling block, the cooling block defining a through-hole into which the first segment and the second segment of the capillary column alternately move.

3. The device of claim 2, wherein the cold zone further comprises at least one fan-heatsink corresponding to the at least one Peltier device.

4. The device of claim 2, wherein the first hot zone comprises a first heated tube, and second hot zone comprises a second heated tube.

5. The device of claim 4 wherein each of the first and second heated tubes are aligned with the through-hole of the cooling block.

6. The device of claim 5 wherein the first segment of the capillary column moves between the first heated tube and the through-hole of the cooling block, and the second segment of the capillary column correspondingly moves between the through-hole of the cooling block and the second heated tube.

7. The device of claim 4 wherein the cold zone further comprises an enclosure housing the cooling block and the at least one Peltier device, the enclosure defining holes corresponding to openings at the ends of the through-hole of the cooling block, the holes in the enclosure being capped with corresponding septums.

8. The device of claim 7, wherein the first and second heated tubes pass through the corresponding septums into the enclosure, and do not contact the cooling block to prevent heat transfer from the first and second heated tubes to the cooling block.

9. The device of claim 4, wherein the first heat source comprises conductive heat from an electrically heated first heated block contacting the first heated tube, and the second heat source comprises conductive heat from an electrically heated second heated block contacting the second heated tube.

10. The device of claim 4, wherein the capillary column is connected to a first dimension column of the GC system at an exterior wall of the GC oven, passes though the first heated block, the first heated tube, the cooling block, the second heated tube and the second heated block, and is connected to a second dimension column of the GC system at the exterior wall of the GC oven.

11. The device of claim 4, wherein the first heated block contains a first loop of the capillary column that increases in size when the first segment of the capillary column moves to the first heated tube and decreases in size when the first segment of the capillary column moves to the through-hole of the cooling block.

12. The device of claim 11, wherein the second heated block contains a second loop of the capillary column that decreases in size when the second segment of the capillary column moves to the through-hole of the cooling block and increases in size when the second segment of the capillary column moves to the second heated tube.

13. The device of claim 4, wherein the first heat source comprises an electric wire coil wrapped around at least a portion of the first heated tube, and the second heat source comprises an electric wire coil wrapped around at least a portion of the second heated tube.

14. The device of claim 1, further comprising:
    a solenoid comprising a movable rod connected to the capillary column to control the movement of the first segment of the capillary column between the first hot zone and the cold zone, and the movement of the second segment between the cold zone and the second hot zone.

15. The device of claim 14, wherein the solenoid comprises a linear solenoid, and the movable rod is configured to move back and forth in a substantially linear direction.

16. The device of claim 14, wherein the solenoid comprises a rotary solenoid, and the movable rod is configured to move back and forth in an arc movement.

17. A dual-stage thermal modulation device for a gas chromatography (GC) system, the device comprising:
- a cooling block and at least one Peltier device abutting the cooling block in an enclosure, the cooling block defining a through-hole having first and second end openings corresponding to first and second holes in the enclosure, the cooling block and the at least one Peltier device being located outside of a GC oven of the GC system;
- a first heated tube having a corresponding first heat source, the first heated tube being aligned with the first hole in the enclosure, such that a first segment of a capillary column passing through the first heated tube is able to move alternately between the first heated tube and the through-hole in the cooling block in accordance with a modulation frequency; and
- a second heated tube having a corresponding second heat source, the second heated tube being aligned with the second hole in the enclosure, such that a second segment of the capillary column passing through the second heated tube is able to move alternately between the through-hole in the cooling block and the second heated tube in accordance with the modulation frequency.

18. The device of claim 17, further comprising:
- a solenoid comprising a movable rod connected to the capillary column to control the movement of the first segment of the capillary column between the first heated tube and the through-hole in the cooling block, and the movement of the second segment between the through-hole in the cooling block and the second heated tube.

19. The device of claim 17, wherein the first and second holes in the enclosure are capped with corresponding septums, the first and second heated tubes passing through the corresponding septums into the enclosure and not contacting the cooling block to prevent heat transfer to the cooling block.

20. A two-dimensional gas chromatography (GC) system, comprising:
- a GC oven comprising an exterior oven wall and containing a first dimension column and a second dimension column; and
- a dual-stage thermal modulator positioned outside the GC oven, the dual-stage thermal modulator comprising:
  - a metal cooling block and at least one Peltier device abutting the metal cooling block, the metal cooling block defining a through-hole having first and second end openings corresponding to first and second holes in the enclosure;
  - a first heated metal tube having a corresponding first heat source, the first heated metal tube being aligned with the end opening of the through-hole, such that a first segment of a capillary column passing through the first heated metal tube is able to move alternately between the first heated metal tube and the through-hole in the metal cooling block in accordance with a modulation frequency;
  - a second heated metal tube having a corresponding second heat source, the second heated metal tube being aligned with the second end opening of the through-hole, such that a second segment of the capillary column passing through the second heated metal tube is able to move alternately between the through-hole in the metal cooling block and the second heated metal tube in accordance with the modulation frequency; and
  - a solenoid comprising a movable rod connected to the capillary column to control the movement of the first and second segments of the capillary column,
- wherein the capillary column is serially connected between the first dimension column and the second dimension column at the exterior oven wall.

\* \* \* \* \*